United States Patent [19]

Anton et al.

[11] Patent Number: 4,689,315

[45] Date of Patent: Aug. 25, 1987

[54] AMORPHOUS SILICA PARTICLES, A METHOD FOR PRODUCING SAME, AND CATALYST THEREOF

[75] Inventors: Octavian Anton, Brussels; Pierre Jacobs, Gooik; Georges Poncelet, Beauvechain; Phillippe Jacques, Ciney, all of Belgium

[73] Assignee: Redco N.V., Kapelle Op Den Bos, Belgium

[21] Appl. No.: 716,695

[22] Filed: Mar. 27, 1985

[30] Foreign Application Priority Data

Apr. 14, 1984 [DE] Fed. Rep. of Germany ....... 3414232

[51] Int. Cl.$^4$ .............................................. B01J 21/08
[52] U.S. Cl. ................................... 502/241; 502/232; 502/242; 502/243; 502/246; 502/250; 502/258; 502/263; 423/335
[58] Field of Search ............... 502/232, 218, 261, 241, 502/243, 242, 250; 423/335, 336

[56] References Cited

U.S. PATENT DOCUMENTS

| | | | |
|---|---|---|---|
| 2,871,200 | 1/1959 | Doumani | 502/218 |
| 3,501,324 | 3/1970 | Kubo | 106/120 |
| 4,330,519 | 5/1982 | Takahashi et al. | 423/335 |
| 4,368,303 | 1/1983 | McDaniel | 502/232 X |

*Primary Examiner*—Carl F. Dees
*Attorney, Agent, or Firm*—Wegner & Bretschneider

[57] ABSTRACT

Amorphous, approximately spherical silica particles prepared by the acidic hydrolysis of an approximately spherical synthetic calcium silicate having a uniform microgranular structure on their external surfaces and a structure in the interior thereof which structure only weakly recall the original crystal needle structure of the starting material. The average external particle size is from 15 to 80 $\mu$m, the apparent particle volume is from 1.3 to 3 cm$^3$/g, and the specific surface area is from 250 to 800 m$^2$/g. The silica particles are particularly suitable for use as catalyst supports.

14 Claims, 5 Drawing Figures

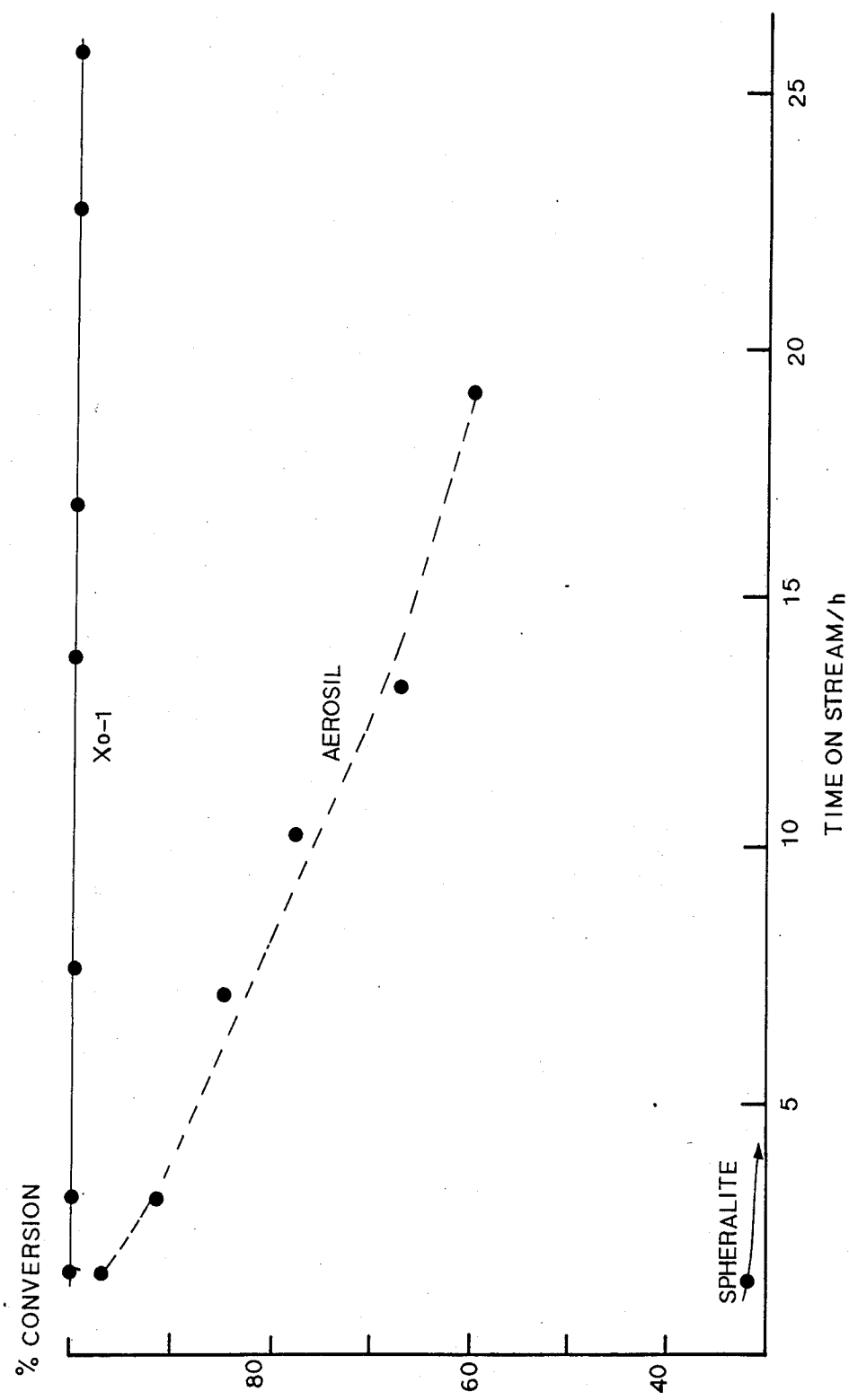
FIG. 3 HYDROGENATION OF NITROBENZENE
5% Ni on support

XONOTLITE PARTICLES
(STARTING MATERIAL)
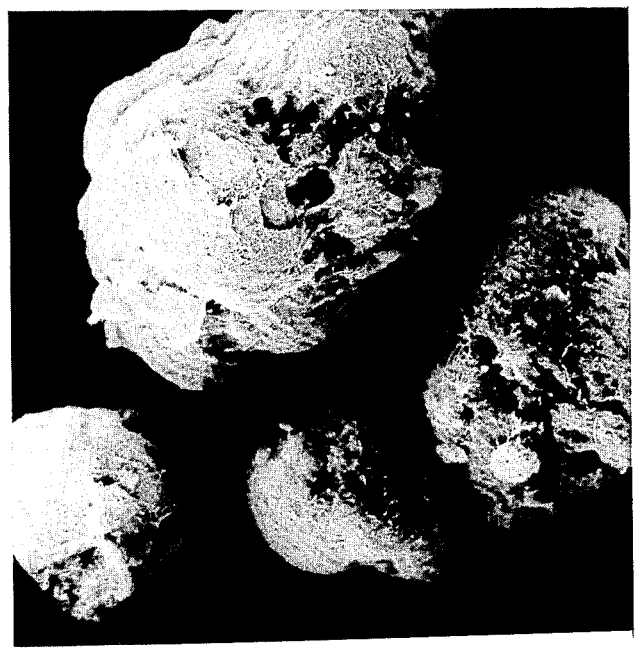
FIG. A(1)
500x   (1cm=20μ)
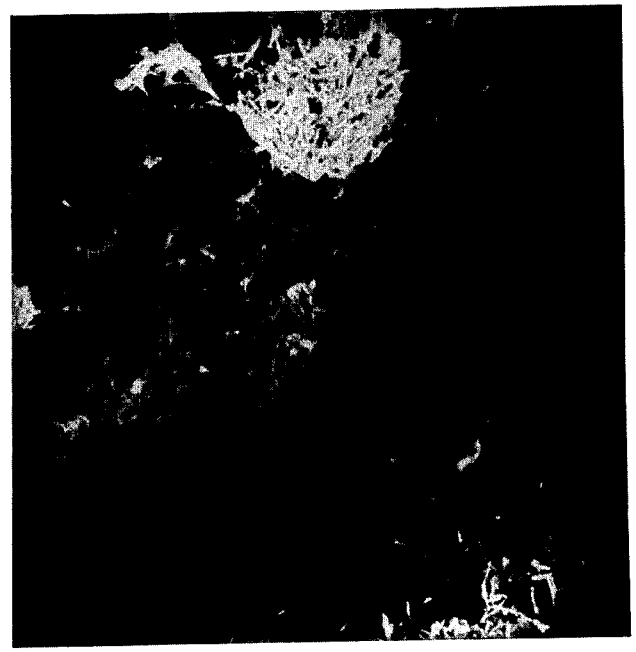
FIG. A(2)
2000x   (1cm=5μ)

SILICA PARTICLES FROM XONOTLITE
(SULFAMIC ACID TREATMENT)
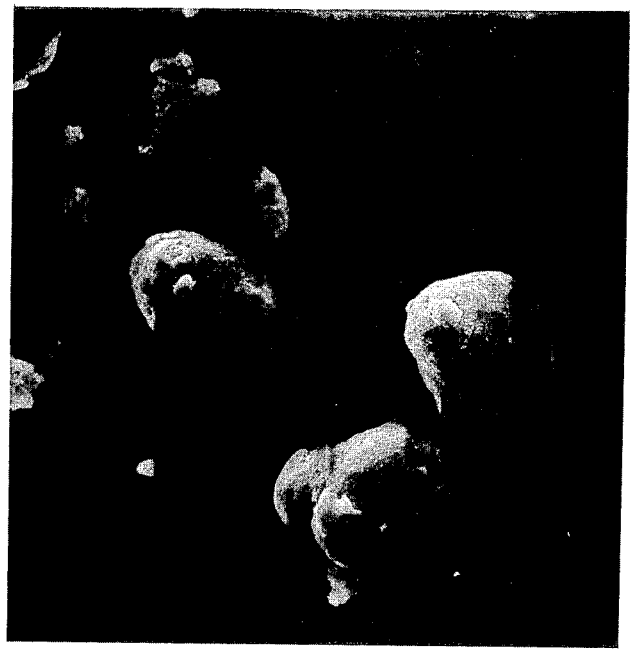
500 x
FIG. B(1)
2000 x
FIG. B(2)
5000 x
FIG. B(3)

AMORPHOUS SILICA PARTICLES, A METHOD FOR PRODUCING SAME, AND CATALYST THEREOF

BACKGROUND OF THE INVENTION

The present invention relates to amorphous, approximately spherical silica particles obtained by the acidic hydrolysis of approximately spherical synthetic calcium silicate particles having a particle size of from 20 to 120 $\mu$m. The invention further relates to a method for producing these silica particles and to a use thereof, more specifically as a support for catalysts.

DISCUSSION OF THE PRIOR ART

Amorphous silica particles may be prepared according to a variety of methods. The particles are used for various purposes; in particular, as a support for catalysts. The preparation of amorphous silica particles in general is achieved by neutralizing aqueous sodium silicate solutions with inorganic acids, such as hydrochloric acid or sulfuric acid. The resulting precipitates are washed and dried. Examples of such preparation methods are described in U.S. Pat. Nos. 2,114,123 and 1,751,955. Further methods for the preparation of amorphous silica particles utilize hydrolysis or flame combustion in the gaseous state. These silicas are commercially available, for example, under the trade names of "Aerosil", "Spherosil", "Cabosil", or "Xerogel". These amorphous silica particles, in general, are of irregular or spherical shape and have different particle sizes, depending on the preparation method and further processing. For certain purposes, finely divided silica particles can be shaped into larger pellets by using suitable binders. For an activation for use as a catalyst support, the silica particles sometimes are calcined.

In British Patent Specification No. 1,511,125, corresponding to German Offenlegungsschrift No. 26 12 281, there are described amorphous silica particles, molded articles having been obtained therefrom, and processes for the preparation thereof. The silica particles described therein are obtained by hydrolyzing synthetic calcium silicates having a particle size of from 20 to 120 $\mu$m with carbon dioxide in the presence of water followed by acid leaching with concentrated hydrochloric acid. The resulting products still completely exhibit the morphology of the crystalline starting material, although they exclusively consist of amorphous silica. Thus, in the course of this two-step acid treatment, the original form of the starting material is retained virtually unchanged. However, the silica thus obtained has a larger porosity and a higher specific surface area than the starting calcium silicate particles. The silica particles thus obtained are usable for various purposes, inter alia, as a support for catalysts.

The above-mentioned silicas produced in the gaseous state are also suitable as supports for catalysts. A drawback inherent to such catalysts is the relatively high price.

The above-mentioned precipitation of amorphous silicas and the neutralization of alkali silicates results in very different products and is reproducible only with difficulties. Often gels which are difficult to filter off and to purify or products with entirely different particle sizes are formed.

In East German Patent Specification No. 0153 107, a process is described for the preparation of a highly dispersed silica wherein a calcium silicate or a calcium silicate hydrate, with thorough mixing and cooling, is treated with an excess of a 5 to 25% mineral acid solution; a product of good quality is obtained in one step. According to this process, extremely finely divided products having a high specific surface area are obtained which can be put into versatile uses. However, the products are too finely divided for use as a catalyst support without being pelletized.

OBJECT OF THE INVENTION

It is an object of the present invention to provide amorphous silica particles that (a) have a sufficient mechanical strength and a high specific surface area, (b) are not too finely divided, (c) have a substantially spherical structure, and (d) are particularly suitable as a catalyst support.

DESCRIPTION OF THE DRAWINGS AND FIGURES

FIG. 3 is a plot of % conversion of nitrobenzene to aniline by hydrogenation vs. time on stream for a nickel supported catalyst in accordance with the present invention and two prior art supports; see Example 5 d2), infra;

Figure 1:
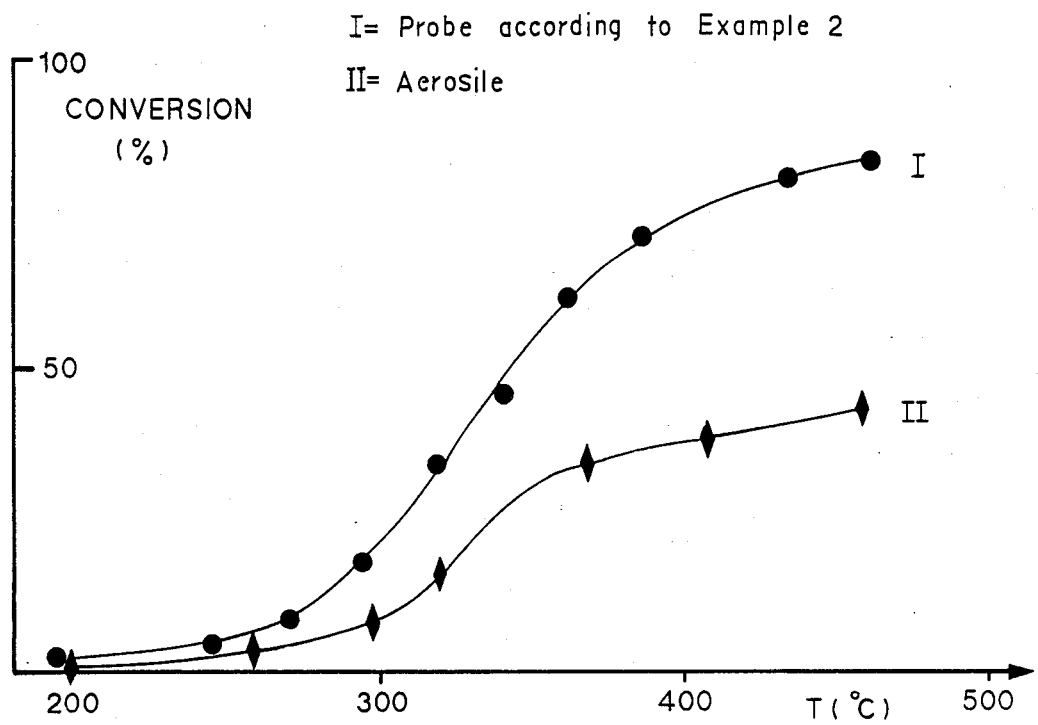
FIG. 1 is a plot of % conversion vs. temperature of a catalyst supported on particles of the present invention and of a comparable catalyst supported on Aerosil 350; see Example 5, infra.

Fig. A depicts the surface structure of particles used as the starting material of the present invention; see Reference Example 1, infra; and Fig. B depicts particles of the present invention as prepared in Example 1, infra.

DESCRIPTION OF THE INVENTION

It has been found that products meeting the objects of the invention are formed, when approximately spherical synthetic calcium silicates having a particle size of from 20 to 120 $\mu$m and a crystal needle structure of interlocking needles of xonotlite, tobermorite, and/or calcium silicate hydrate (hereinafter "CSH") crystals are hydrolyzed at room temperature or a slightly elevated temperature at a pH of from 0.6 to 3.0, preferably from 0.8 to 2.2 and most preferred 1.0 to 1.8, with an acid that does not form a sparingly soluble calcium salt.

These starting materials can be made according to, for example, U.S. Pat. No. 3,501,324 and EP-publication No. 0 009 836.

Suitable acids therefore are, more specifically, strong to medium organic or inorganic acids. Sulfamic acid, benzenesulfonic acid, p-toluenesulfonic acid, 5-sulfosalicylic acid, 4-toluidinesulfamic acid, sulfanilic acid, or mixtures thereof have proven to be particularly suitable. However, maintaining the pH range is of crucial importance, as only then products will be obtained that have a uniform micro-granular (and apparently closed surface) and, in the interior thereof, have a structure that only weakly recalls the original crystal needle structure of the starting material. With pH values of more than 3, the original structure is completely retained as, for example, is observed upon the hydrolysis with carbonic acid according to British Patent Specification No. 1,511,125. At a pH value below 0.6, on the other hand, the original structure is completely destroyed so that products corresponding to those of East German Patent Specification No. 0153 107 are obtained. Surprisingly, it is possible, in the pH range of from pH 0.6 to pH 3, to make a product according to this invention. During the process according to the invention the spherical aggregates of the starting material of from 20 to 120 μm shrink to an average external particle size of from 15 to 80 μm. This conforms to a degree of shrinkage of about 30 to 50%. During this shrinkage, the structure of the silica is compacted as compared to the structure of the starting material, so that the apparent particle volume of the starting material (amounting to 3.2 to 5.6 cm$^3$/g) is lowered to 1.3 to 3.0 cm$^3$/g. (The term "apparent particle volume" expressed in cm$^3$/g is the reciprocal of apparent bulk density (expressed in g/cm$^3$), a well-known expression in powder technology. The apparent particle volume was used for the experiments to compare volumes of given weights of powder). However, surprisingly, the specific surface area of the compacted silica particles has been increased by a multiple. Thus, the spherical silica particles according to the invention have a specific surface area of from 250 to 800 m$^2$/g, normally 300 to 600 m$^2$/g, while they have an amorphous structure. The external surface has a continuous fine-grain, but nevertheless amorphous, structure, and in the interior there is found a structure that is also amorphous, which, however, still weakly recalls the original crystal needle structure of the starting material. By this is meant that the internal texture has conserved the memory of the original primary needle-shaped crystals but the latter are considerably altered and are now coated with a layer of amorphous material.

Another surprising effect consists in that, in spite of the shrinkage and change in texture, the soluble calcium salts can be easily washed out and the obtained product can be filtered off without any trouble.

The reasons for these unexpected results so far are not known. More specifically, there is still no explanation as to why these results are only obtained within the relatively narrow pH range of from 0.6 to 3, and preferably from 0.8 to 2.2.

Thus, in a first aspect, it is an object of the present invention to provide amorphous, approximately spherical silica particles obtained by the acidic hydrolysis of an approximately spherical synthetic calcium silicate having a particle size of from 20 to 120 μm, characterized in that they have an average external particle size of from 15 to 80 μm, an apparent particle volume of from 1.3 to 3 cm$^3$/g, and a specific surface area of from 250 to 800 m$^2$/g.

The amorphous silica particles according to the present invention may also be characterized by that they have a uniform microgranular structure on the external surface thereof and a structure in the interior thereof which structure only weakly recalls the original crystal needle structure of the starting materials. Thus, approximately spherical synthetic calcium silicates of a size from 20 to 120 μm are used as the starting materials, the needle structure of which consists of interlocking needles of xonotlite, tobermorite, and/or CSH crystals.

The preparation of synthetic crystalline calcium silicates has been described, for example, in the U.S. Pat. No. 3,501,324 and in European Offenlegungsschrift No. 0 009 836. These products are marketed, among others, by the Promat Company, Dusseldorf, West Germany and are sold under the trademark "Promaxon". They are used, in the first place, for thermal insulation. A further use thereof has been described in British Patent Specification No. 1,511,125 which teaches that spherical silica particles having a very loose structure are formed by acidic hydrolysis with carbon dioxide in the presence of water followed by acid leaching with concentrated hydrochloric acid.

It is another object of the present invention, thus, to provide a process for the preparation of particles by the acidic hydrolysis of synthetic calcium silicates having a particle size of from 20 to 120 μm. The process is characterized in that the calcium silicates are hydrolyzed in the pH range of from 0.6 to 3.0 at room temperature (or a slightly higher or lower temperature) with an acid that does not form a sparingly soluble calcium salt, the insoluble silica particles are separated, washed out with water and dried. Preferably the process is carried out at a pH from 0.8 to 2.2. In the practice of the present invention, a pH of from 1.0 to 1.8 has proven to be most preferable.

The temperature normally should be chosen between 0° and 60° C. The temperature mainly influences the velocity of the reaction.

In carrying out the present process, strong or medium organic or inorganic acids are suitable. Preferred as particularly suitable are sulfamic acid, benzenesulfonic acid, p-toluenesulfonic acid, 5-sulfosalicylic acid, 4-toluidinesulfamic acid, sulfanilic acid, or mixtures thereof.

The amorphous, approximately spherical silica particles according to the invention and prepared according to the invention may be employed for various purposes. They are particularly suitable for use as a catalyst support. The catalysts to be considered are, more specifically, metal catalysts selected from one or more metals of the groups Ib, IIb, IIIb, IVb, Vb, VIb, VIIb, and VIII of the Periodic Table. Surprisingly good results were achieved with catalysts containing one or more metals of the group of platinum, palladium, nickel, and ruthenium.

Further surprisingly good results were achieved with the use of the silica particles according to the invention as supports for enzymes and as supports for covalent bound enzymes.

Since the silica particles according to the present invention are superior to those previously known with respect to their density, surface structure, and mechanical abrasive strength, they are also well usable for other conventional uses of silicas. Thus, they are usable as fillers, drying substances, absorbents, deodorants, filter aids, heat-stable filters, additives for adhesives, heat-protecting agents, delustering agents in the paper industry, emulsifiers for cosmetics, abrasionresistant agents, heat insulators, viscosity-controlling agents, pigments, tooth paste, carriers for agricultural chemicals and pharmaceuticals, absorbents for gas chromatography, molecular sieves, and shaped articles.

The silica particles according to the invention, the process for preparing same, and the preferred uses thereof are further illustrated by the following examples:

REFERENCE EXAMPLE 1

(Preparation of the Starting Material)

Quicklime or a hydrated lime with a calcium oxide content of 95% and crystalline silica having a purity of 95% SiO$_2$ are mixed in water in a molar ratio of 0.94:1 to prepare a suspension having a water to solids ratio of 11:1. The suspension is stirred in an autoclave at a temperature of about 190° C. Xonotlite crystals are obtained as a suspension after 8 hours. This suspension is partially dewatered by filtration. The resulting product has the following properties:

Morphology: Spherical particles comprising three-dimensionally randomly interlocking primary crystals;
Diameter: 20 to 120 μm;
Apparent particle volume: 5.6 cm$^3$/g;
Specific surface area: 60 m$^2$/g;
Surface structure: random network of fine interlocking crystals. Typical particles are shown in the photographs of the attached FIG. A.

EXAMPLE 1

(Extraction of Calcium)

Xonotlite (50 g) made according to Reference Example 1 (dry weight basis of 110° C.) is dispersed in 2,000 ml of demineralized water; a 1N sulfamic acid solution is added. The acid is rapidly added in an amount so that the pH of the suspension is about 1.3. The suspension is continuously stirred at room temperature. With an increasing degree of neutralization, the pH will rise again so that further acid has to be added in order to maintain the pH range at from 1.4 to 1.6. After 30 minutes, there had been added about 1,000 ml of the acid solution, and the pH was stabilized at 1.5. It remained at this value for at least 24 hours. Thereafter, the slurry is dewatered by filtration and thoroughly washed with water to remove the resulting calcium sulfamate salt. Then the product is dried. The resulting solid product consisting of amorphous silica particles had the following properties:

Morphology: Spherical particles having a smooth surface structure comprising an external shell and an internal core that still contains residues of pseudo-crystals;
Diameter: 30 to 70 μm;
Apparent particle volume: 3 cm$^3$/g;
Specific surface area: 350 m$^2$/g;
Chemical composition: more than 99.5% of SiO$_2$.
Typical particles are shown in the photographs of FIG. B.
The material having been thus obtained may be used, for example, directly as a catalyst support.

EXAMPLE 2

(Preparation of a Platinum Catalyst)

The product according to Example 1 was impregnated with an aqueous solution of a platinum salt (Pt(NH$_3$)$_4$Cl$_2$) corresponding to 2% by weight of platinum metal. The thus-obtained impregnated solid product was heated under oxygen at 450° C. and then reduced with hydrogen at 450° C. Thereby a platinum having been uniformly distributed on the support was obtained.

For comparison purposes a commercially available silica (Aerosil 350) was used as the support.

EXAMPLE 3

(Preparation of a Nickel Catalyst)

Silica particles according to Example 1 were impregnated with an aqueous solution of nickel nitrate, whereby 2% by weight of nickel was deposited on the carrier. The thus-obtained impregnated solid product was thermally treated under oxygen at 550° C. and then reduced with hydrogen at 450° C. A nickel supported catalyst was obtained.

For comparison purposes, a commercially available silica (Aerosil 350) was used as the support.

EXAMPLE 4

(Preparation of a Ruthenium Catalyst)

Silica particles according to Example 1 were impregnated with an aqueous solution of ruthenium chloride (RuCl$_3$), whereby 5% by weight of ruthenium was deposited on the carrier. The thus-obtained solid product was reduced in hydrogen at 500° C., whereby a ruthenium supported catalyst was obtained.

For comparison purposes, a commercially available silica (Aerosil 350) was used as the support.

EXAMPLE 5

(Test of the Prepared Metal Catalysts)

Fixed bed reactors were filled with equal volumes of the catalysts and comparative catalysts obtained according to the Examples 2, 3, and 4 (0.6 ml each). The charges contained either 220 mg of metal on the silica according to the invention or 350 mg of metal on Aerosil 350, respectively. Hydrocarbons in the gaseous state were passed through the reactors, viz. 32 ml of n-decane, 92 ml of hexane, and 105 ml of benzene per ml of catalyst and per hour. The reaction temperature was raised in steps and then held constant. Sampling was performed at each step on stream after 1.45 hours. The reaction products were analyzed by gas chromatography, the data including the total conversion (%) and the percent distribution of the various fractions of reaction products.

(a) Dehydrocyclisation

Platinum-loaded catalysts according to Example 2 were used for a dehydrocyclisation of n-decane. The temperature range was from 242° C. to 475° C. The results were almost identical and showed that the catalyst prepared according to the invention with a reduced metal amount is capable of the same performance as a catalyst based on Aerosil 350 employing a higher amount of metal.

(b) Hydrogenolysis

The nickel-loaded catalysts according to Example 3 were used for an investigation of the hydrogenolysis of n-decane. The temperature ranged from 242° C. to 306° C. The results showed that with the catalyst prepared according to the invention at a temperature lower by an average of from 15° C. to 25° C. the same results could be achieved as by using a catalyst based on Aerosil 350.

(c) Reforming

The two platinum-loaded catalysts according to Example 2 were used for reforming n-hexane. The temperature range was from 200° C. to 460° C. The results are shown in the graph of FIG. 1.

(d1) Hydrogenation of benzene

Two nickel-loaded catalysts according to Example 3 were used to hydrogenate benzene into cyclohexane, viz. in the temperature range of from 40° C. to 200° C. The results show that the catalyst prepared according to the invention hydrogenates faster and at lower temperature. More specifically, at 100° C. the conversion is 95% whereas a catalyst based on Aerosil 350 yields only 5%.

(d2) Hydrogenation of nitrobenzene

A nickel supported catalyst was prepared according to Example 3, using 5% instead of 2% by weight of nickel. For comparison a commercially available support (silica, Aerosil 350 or alumina, Spheralite SAP350) was also prepared.

These catalysts were used in the vapor phase hydrogenation of nitrobenzene to aniline in the following experimental conditions: a weight hourly space velocity in nitrobenzene of 4.1 $h^{-1}$ (g reactant per g catalyst and per h), a hydrogen/nitrobenzene ratio of 95/1, and a reaction temperature of 100° C. The conversion of the reactant was monitored continuously in a tubular flow reactor. In the reaction conditions used, aniline was the only product formed. The conversion on the three supports containing equal amounts of nickel is shown in FIG. 3. It follows that the activity of the nickel on alumina catalyst is very low; the two silica supports (Aerosil and the one prepared according to the invention) are initially very active. The Aerosil-based catalyst deactivates in time, however, while the catalyst of the invention shows a stable activity.

(d3) Hydrodealkylation of toluene

A catalyst consisting of 5 wt % cobalt on Aerosil 350 (cata I) and on the support prepared according to the present invention (cata II) were prepared in the same way as the supported nickel catalysts of Example 3. They were used in the hydrodealkylation reaction of toluene to benzene at 300° C., using a weight hourly space velocity of 0.65 $h^{-1}$ and a $H_2$/toluene molar ratio of 1.6. In those conditions, the conversion of toluene to benzene was 90% on cata II, while on cata I it was only 62%.

(d4) Dehydrogenation of i-propanol

The dehydrogenation of i-propanol to acetone on cata I and II was measured at 260° C., using a weight hourly space velocity of 0.3 $h^{-1}$. The conversion on cata I was 52%, while on cata II, it amounted to 89%.

Comparative Examples

The properties of nickel catalysts on various silica supports were investigated with respect to the employed extraction methods. The xonotlite product according to Reference Example 1 was treated in four different manners.

Sample 1 was prepared according to the invention with sulfamic acid at a controlled pH value in accordance with Example 1.

Sample 2 was prepared by using 1 N sulfamic acid; however, the pH was not controlled. The acid was added at a constant rate. During said procedure significant variations of pH were observed.

Sample 3 was treated with a weak organic acid (acetic acid). In this case, even by means of a rapid addition of the acid, the pH could not be adjusted into the pH range according to the invention.

Sample 4 was treated according to the British Patent Specification No. 1,511,125 first with carbon dioxide in the presence of water and then with concentrated hydrochloric acid.

Figure 2:
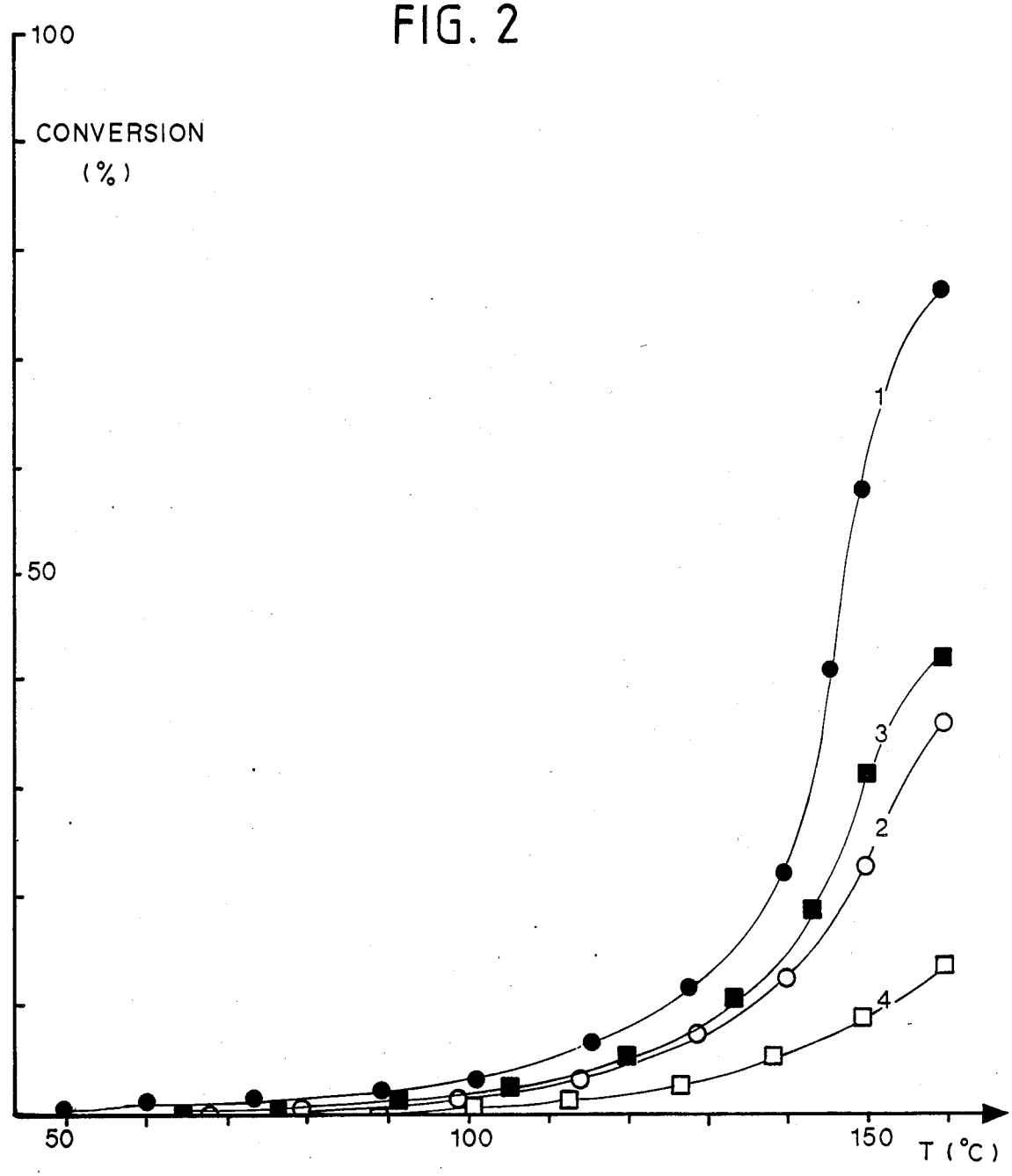
FIG. 2 is a plot of % conversion vs. temperature of supported nickel catalysts corresponding to Samples 1 to 4; see the Comparative Examples, infra.

All of the samples, upon extraction with water, were washed, filtered, dried, and then loaded with nickel in accordance with the procedure of Example 3 using 5% by weight of nickel instead of 2%. The catalysts were tested according to Example (5 d) with a space velocity of 60 g of benzene per g of catalyst and per hour. The temperature range was chosen between 50° and 160° C. The relative catalytic activities are shown in FIG. 2.

The above Examples demonstrate that only the catalyst support prepared according to the invention exhibits the surprisingly good properties and that these properties depend on the preparation process for the support according to the invention.

What is claimed is:

1. Amorphous, approximately spherical silica particles obtained by the acidic hydrolysis of an approximately spherical synthetic calcium silicate having a particle size of from 20 to 120 $\mu$m, said silica particles having an average external particle size of from 15 to 80 $\mu$m, an apparent particle volume of from 1.3 to 3 $cm^3/g$, and a specific surface area of from 250 to 800 $m^2/g$.

2. The amorphous silica particles of claim 1, further having a uniform microgranular structure on the external surface thereof and a structure in the interior thereof, which structure has conserved the memory of the original primary needle-shaped crystal structure with physical modification due to shrinkage and the coating of the interior crystals with a layer of amorphous material.

3. The amorphous silica particles of claim 1, wherein the original crystal structure of the starting material consists of interlocking needles of xonotlite, tobermorite, and/or calcium silicate hydrate crystals.

4. The amorphous silica particles of claim 2, wherein the original crystal structure of the starting material consists of interlocking needles of xonotlite, tobermorite, and/or calcium silicate hydrate crystals.

5. A method for preparing amorphous, approximately spherical silica particles having an average external particle size of from 15 to 80 $\mu$m, an apparent particle volume of from 1.3 to 3 $cm^3/g$, and a specific surface area of from 250 to 800 $m^2/g$ comprising
    subjecting to acidic hydrolysis an approximately spherical synthetic calcium silicate having a particle size of from 20 to 120 $\mu$m, said acid hydrolysis being carried out at a pH range of from 0.6 to 3.0 at approximately room temperature with an acid that does not form a sparingly soluble calcium salt,
    separating the resulting insoluble silica particles, washing the separated particles with water, and drying the washed particles.

6. The method of claim 5, wherein hydrolysis is carried out at pH of 0.8 to 2.2.

7. The method of claim 6, wherein said acid is a strong to medium organic or inorganic acid.

8. The method of claim 7, wherein said acid is sulfamic acid, benzenesulfonic acid, p-toluenesulfonic acid, 5-sulfosalicylic acid, 4-toluidinesulfamic acid, sulfanilic acid, or a mixture thereof.

9. A supported catalyst comprising a catalytically effective amount of a catalyst supported on the amorphous silica particles of claim 1.

10. The supported catalyst of claim 9, wherein said amorphous silica particles further have a uniform microgranular structure on the external surface thereof and a structure in the interior thereof, which structure has conserved the memory of the original primary needle-shaped crystal structure with physical modifications due to shrinkage and the coating of the interior crystals with a layer of amorphous material.

11. The supported catalyst of claim 9, wherein the original crystal structure of the starting material consists of interlocking needles of xonotlite, tobermorite, and/or calcium silicate hydrate crystals.

12. The supported catalyst of claim 9, wherein said catalyst is a metal selected from one or more metals of the groups Ib, IIb, IIIb, IVb, Vb, VIb, VIIb, and VIIIb of the Periodic Table.

13. The supported catalyst of claim 12, wherein said metal is selected from one or more metals of the group of platinum, palladium, nickel, and ruthenium.

14. The supported catalyst of claim 9 comprising a catalytically effective amount of an enzyme and/or biocatalyst supported on the amorphous silica particles of claim 1.

* * * * *